United States Patent [19]

Lund

[11] 4,314,062

[45] Feb. 2, 1982

[54] PROCESS FOR PRODUCTION OF DICYANOPIPERAZINE

[75] Inventor: Richard B. Lund, Jackson, Ala.

[73] Assignee: Ciba-Geigy Corporation, Ardsley, N.Y.

[21] Appl. No.: 140,535

[22] Filed: Apr. 15, 1980

[51] Int. Cl.$^3$ .............................................. C07D 295/10
[52] U.S. Cl. .................................... 544/402; 544/388
[58] Field of Search ........................................ 544/402

[56] References Cited

FOREIGN PATENT DOCUMENTS 1309832  3/1973  United Kingdom .

OTHER PUBLICATIONS

Baker, "Chemical Abstracts", vol. 75, 1971, Col. 140886s.
Lambert, et al., "Chemical Abstracts", vol. 76, 1972, Col. 112527c.

Primary Examiner—Donald G. Daus
Assistant Examiner—James H. Turnipseed
Attorney, Agent, or Firm—Karl F. Jorda

[57] ABSTRACT

This invention relates to the manufacture of dicyanopiperazine. More particularly, it relates to inexpensive, ecologically desirable procedures based on the controlled reaction of piperazine with a cyanogen halide in water.

8 Claims, No Drawings

PROCESS FOR PRODUCTION OF DICYANOPIPERAZINE

BACKGROUND

Dicyanopiperazine is a useful compound due to its active cyano-groups. It is an intermediate in the manufacture of biguanide antibiotics as described in British patent specification No. 1,309,832 which also includes descriptions for the synthesis of substituted cyanamides by the reaction of secondary amines with cyanogen halides in the presence of ammonia according to Equation (I):

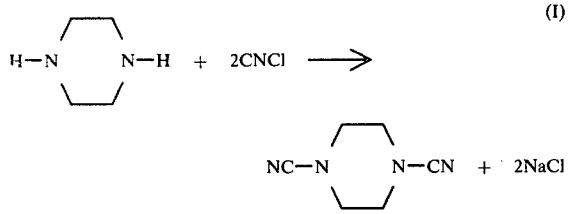
(I)

As pointed out therein, problems arise in this reaction due to the well known tendency of ammonia and amines to react with cyanogen halides to form cyanamides according to the Equation (II):

$$CNCl + NH_3 \rightarrow CN.NH_2 + HCl \quad (II)$$

The yields according to the process described in these references are only in the range 87 to 93% and require the use of ammonia. The ammonium chloride by-product presents disposal problems.

It is an object of this invention to provide a process for the preparation of dicyanopiperazine in high yield in the range 97 to more than 99% and of high purity of at least 96%. It is further object to provide a process that utilizes less expensive reaction components and is conducted in a medium wherein the final by-products to be disposed are ecologically acceptable.

THE INVENTION

The invention is a process for the preparation of dicyanopiperazine which comprises the steps of adding two moles of a cyanogen halide to each mole of piperazine dissolved in water, reacting the mixture at a temperature of at least 10° C., but below about 60° C., maintaining the pH of the mixture during the resulting reaction within the range 6.0 to 9.0 by the addition of an alkali metal hydroxide source; cooling the resulting slurry of dicyanopiperazine in salt water to a temperature below about 10° C.; and filtering the dicyanopiperazine from the saline spent reaction medium.

DETAILED DESCRIPTION

The preferred cyanogen halide is cyanogen chloride because of its greater reactivity, low cost and ready availability. Cyanogen bromide or iodide may also be used.

The preferred alkali hydroxide source is sodium hydroxide (NaOH) because it is inexpensive and its final reaction product, NaCl, can be safely disposed of in an acceptable manner. Potassium hydroxide (KOH) is acceptable but provides no advantage over NaOH. Sodium carbonate ($Na_2CO_3$) can be used but, because it releases $CO_2$ during the neutralization reaction, causes complications in disposal of the released $CO_2$ which overrides its slightly lower cost. The effervescence also causes mechanical difficulties in containing the foam and lowers the yield.

Piperazine, in solution in the initial reaction mixture, generates a pH of about 11 to 12. Upon reaction with cyanogen chloride, two molecules of HCl are liberated per mole of dicyanopiperazine that is formed. Consequently the pH of the reaction mixture decreases rapidly. However in the acid solution, when the pH is allowed to fall to below about 6.0, the dihydrochloride salt of piperazine is formed and the reaction with cyanogen chloride becomes slower. Consequently, some cyanogen chloride is lost by side reaction with water to liberate cyanic acid and HCl according to the following reaction:

$$CNCl + H_2O \rightarrow HNCO + HCl$$

By controlling the pH above 6.0 free piperazine is present to react rapidly with cyanogen chloride and the above side reaction with water is minimized.

However, the order of reactivity of CNCl is piperazine >> hydroxyl ion >> water. At pH above about 8 and particularly above about 12 the side reaction of the CNCl with alkali causes lowered yields. The alkali base used as the acid acceptor to neutralize the HCl released by the desired reaction is not critical provided that the strong base is not present in excess. By adding the NaOH during the reaction is required to maintain the pH within the range 6.0 to 9.0, the reaction is properly controlled and optimized. The addition of NaOH from concentrated solution (about 30 to 50% NaOH) is started as the initial pH decreases to about 6.0 as the CNCl is added. At the start of CNCl addition the pH is about 11 to 12 due to the piperazine basicity alone. The pH in the mixture is followed by instruments and, as it falls toward 6.0, the addition of NaOH is started and controlled to maintain the pH within the range 6.0 to 9.0 but preferably within the range 7.0 to 8.0.

When attempts were made in batch processing to initially add the entire calculated amount of NaOH before the addition of cyanogen chloride was started the yields were low, below 50%.

The preferred agent for adding the CN-groups is cyanogen chloride, but the class of cyanogen halides will serve including specifically cyanogen bromide and cyanogen iodide. It is preferred that the cyanogen halide be free from excess of the halogen used in its preparation. It was noted that dicyanopiperazine manufactured with cyanogen halides having some free halogen had a tendency to yellow on storage. Further such dicyanopiperazine forms dark melts which remain dark after resolidification. The cyanogen halides can be freed from the halogen by conventional methods before use in the process. Cyanogen chloride can be freed from chlorine by distillation by taking advantage of the differences in boiling points between chlorine and cyanogen chloride (−34° C. and +13° C. respectively). When only small amounts of chlorine are present it can be removed by the presence of sodium sulfite in the reaction mass according to the equation (III):

$$Cl_2 + Na_2SO_3 + H_2O \rightarrow 2NaCl + H_2SO_4 \quad (III)$$

The piperazine is used either in the anhydrous form or as the hexahydrate. When the piperazine is available in the form of acid addition salts (monohydrochloride or sulfate) the acid salt must be neutralized to the free base before the cyanogen chloride is added.

The reaction temperature is not critical. At lower temperatures the reaction is still rapid but the solubility of piperazine and dicyanopiperazine decreases and the mixture becomes very thick. Temperatures as low as 10° C. are satisfactory although temperatures less than about 25° C. are less desirable because special refrigeration equipment is required for cooling. Temperatures up to about 60° C. are satisfactory but high temperatures lead to lower yields due to hydrolysis of the dicyanopiperazine according to the following equation:

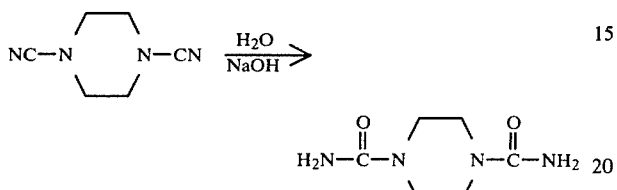

A temperature range of about 25–55° C. is entirely satisfactory for ease of mixing, reduced cooling requirements and high yields. A temperature range of about 30–50° C. is especially preferred and given the highest yields.

The reaction between the cyanogen halides and the piperazine is exothermic and cooling should be used to maintain the reaction mixture within the stated limits. The higher temperatures within the stated range are preferred as they permit the use of more concentrated solutions of the reactants, piperazine and caustic.

Soon after the cyanogen chloride addition in gaseous form is begun, the dicyanopiperazine begins to come out of solution and forms a slurry in the reaction mix. As the reaction proceeds the slurry becomes more concentrated. When the stoichiometric addition of cyanogen chloride is completed, the slurry is cooled before filtration to minimize solubility losses. The solubility of dicyanopiperazine in the saline reaction solution (4 to 20% NaCl in water) is very low at temperatures below about 5° C.

Thus the slurry should be cooled to the range −5 to +5° C., then held at this temperature until the crystallization from the liquid is completed and then filtered. To ensure purity of the product, the filter cake may be washed with pure water. To prevent undue product losses, the wash water should also be cooled below +5° C. The slightly saline wash water may be recycled as solvent for the piperazine or the NaOH.

As the product, dicyanopiperazine, is a mild irritant, it is preferred that the crystal size be large enough to prevent dusting during handling. Previous processes have used ethanol as the reaction solvent because of the excellent solubility of piperazine therein but the product was formed as small crystals. The process of this invention uses water as the sole solvent. An advantage of this solvent aside from cost is that because of the great difference in solubility of the product in warm (35° C.) and cooled (+5° C.) solutions, the product is recovered on cold filtration in a crystal size that is substantially free from dusting. These crystals by NMR have high purity (99+%). The salt (NaCl) solution by-product is readily washed from the crystals with cold water. The filtrate, consisting of the salt water solution in the range 4 to 20% NaCl, can be readily disposed in an ecologically acceptable manner. By comparison, the use of ammonia in the prior art process provides ammonium chloride as the by-product. However, ammonium chloride is unacceptable for direct effluent disposal. The ammonia must be separated from the salt but not released into the environment. This requires expensive equipment.

The process according to this invention may be practiced either by a batch or continuous procedure.

Batch Process

The batch process is carried out by adding a piperazine solution to a reaction vessel provided with a cooling jacket and introducing a stream of gaseous cyanogen chloride below the level of the liquid. The pH of the reaction mixture is followed and when the pH falls towards 7.0, an aqueous solution of NaOH is added. The NaOH and cyanogen addition rates are varied as required to maintain the pH in the range 7.0 to 8. The cooling jacket is activated to keep the temperature of 25° to 50° C. As the required addition of cyanogen chloride is completed, the resulting slurry is cooled to a temperature below about 5° C., preferably in a stirred crystallizer. The cooled slurry is then filtered, the crystallized filter cake is washed with cold water and the product is then dried. The product assays about 99+% and is recovered in yields of better than 97% based on piperazine used.

Continuous Process

The process of this invention lends itself to continuous manufacture. Cyanogen chloride is regularly available from continuous reactors. In addition, the overall reaction of equation I is well suited for continuous processing as the chemical reactions are rapid and the process control is relatively simple. To carry out the continuous processing according to the invention, stock aqueous solutions of piperazine and NaOH (5.0 and 10.5 moles respectively) are prepared. The solutions at temperatures in the range 40–50° C., to keep the piperazine dissolved, are continuously pumped into a stirred reactor. The cyanogen chloride is introduced by dip-tube to the solutions in the reactor. The reactor cooling jacket is activated to maintain the mixture in the vessel in the range 30–35° C. The rate of addition of NaOH is regulated as required to maintain the pH in the range 7.0 to 8.0 by a pH meter. The slurry resulting from the reaction is continuously pumped into a stirred crystallizer where the slurry is cooled to −5 to +5° C.

The cooled slurry is then fed to a continuous filter on which the filter cake of dicyanopiperazine is washed with cold water. The washed filter cake is then dried and recovered. The saline filtrate may be sewered as it contains less than 0.3% dicyanopiperazine.

In a variation of the continuous process the feed consists of a single solution of piperazine with a stoichiometric amount of NaOH dissolved in water. This solution is pumped into a reactor fitted with a cooling jacket. The cyanogen flow to the reactor is adjusted as required to maintain the pH of the reaction mixture in the measured pH range 6–9, preferably 7–8. By this procedure correct reaction stoichimetry is automatically assured because the stoichiometric amount of NaOH is added to the reactor with the piperazine. There is no need to weigh the amount of cyanogen chloride introduced since the amount used is controlled by the amount of piperazine and NaOH initially introduced. Any unconsumed CNCl is bubbled through a scrubber containing 5% NaOH and decomposed.

It should be noted that this type of control is not possible in batch operations. When all the caustic was added at the start of the batch procedures the initial pH was much too high (12-14) for prolonged contact and low yields resulted. This does not happen in the continuous process where the total combined residence time in the reaction vessel and crystallizer averaged 36 minutes.

From the above it can be seen that the unforeseen superior yields and high purity result from the reaction of piperazine with the cyanogen chloride within the temperature range 25-55° C. and controlled within the pH range 6.0-9.0 and, upon completion of the reaction, rapidly cooling the product in the spent medium to below 5° C. and then separating the product from the medium at or below that temperature. At pH above or below the stated reaction range, the purity of the product is compromised. Similarly by rapidly cooling the product it is conveniently covered from the spent medium in excellent yield with minimum loss in the medium. Also, by such complete recovery the spent medium is sufficiently free of the irritant products so that the spent medium (salt solution) can be safely sewered.

The invention, in its preferred modes, will be apparent from the appended examples which illustrate these modes and variants thereof. While exemplary of the invention they are not intended to limit the invention to their illustrated scope. All the art recognized equivalents are intended. The limits of this invention are set forth in the appended claims.

EXAMPLE 1

A round bottom flask is fitted with a stirrer, thermometer, pH electrode, condenser, dropping funnel, gas inlet tube and a scrubber containing 5% HCN. The flask is charged with 290 g of water and 64.5 g of piperazine (0.75 mole). The mixture is warmed to 30° C. to dissolve the piperazine. Through the gas inlet tube extending below the liquid level, 92.7 g of cyanogen chloride (1.52 mole) is slowly bubbled into the liquid. The flask is constantly cooled to maintain the temperature at 30-35° C. The cyanogen chloride addition is completed within two hours. During the CNCl addition the pH of the reaction mixture is monitored and controlled within the range pH 7.0 to 7.5 by the addition of 210 g NaOH in 30% aqueous solution (1.58 mole) via the dropping funnel. The NaOH addition is started after the initial pH of 11.4 drops below 7.5. After the CNCl addition is complete, the mixture in the flask is cooled to 0° to 5° C., stirred for about 15 minutes and the slurry is filtered on a suction filter, (wet cake—122.1 g). The cake is dried at 60° C. in a vacuum oven. Yield 99.4% of theoretical, m.p. 167.5-168.5° C. and 99+% purity by NMR.

EXAMPLE 2

The procedure as described in Example 1 was repeated using CNBr in an equivalent amount. The resultant product was equivalent in yield and purity.

EXAMPLE 3

Into a 3 liter reactor fitted with a gas inlet tube, a stock solution of 430 g piperazine in 2000 g of water heated to 40-50° C. is introduced by a dropping tube at the rate of 6 ml/min. When the level in the reactor covers the gas inlet tube the gaseous CNCl flow via the inlet tube is started. The pH in the reactor is monitored and a 50% NaOH solution is added, as required, to maintain the mixture at a pH in the range 7.0 to 7.5. The reactor is cooled to maintain the mixture at 30-45° C. When the reactor is half full, a discharge pump is activated to maintain the liquid level. The discharge of reaction mixture is collected in a stirred crystallizer where it is cooled to −5 to +5° C.

When the crystallizer is half full the slurry is pumped unto a suction filter. The pump rate is adjusted to maintain the half-way level in the crystallizer. The filter cake is washed with water to 10% of filtrate volume. The process is continued until all the piperazine solution is added.

The filter cake after washing is dried in a vacuum drier. The dried cake is 672.2 g of dicyanopiperazine (98.4% pure) representing a yield of 98.9%. m.p. 167.5-168.5° C. (colorless melt).

EXAMPLE 4

The apparatus of Example 3 was used but was charged from a stock solution comprising 840 g. of 50% NaOH, 430.8 g piperazine and 2000 g of water. This solution was charged at the same rate as in Example 3. It was not necessary to monitor the pH during the reaction. The yield was equivalent to that obtained in Example 3.

What is claimed is:

1. A process for the preparation of dicyanopiperazine which comprises the steps of adding two moles of a cyanogen halide to each mole of piperazine dissolved in water at a temperature of at least 10° but below about 80° C., maintaining the pH of the mixture during the resulting reaction within the range 6.0 to 9.0 by the addition of an alkali metal hydroxide source; cooling the resulting slurry of dicyanopiperazine in salt water to a temperature below about 10° C. and filtering the dicyanopiperazine from the saline spent reaction medium.

2. The process according to claim 1 wherein the cyanogen halide is cyanogen chloride.

3. The process according to claim 2 where the cyanogen chloride is added to the solution maintained at a temperature in the range 25° to 55° C.

4. The process according to claim 3 wherein said hydroxide source is sodium hydroxide added to the mixture to maintain the pH therein within the range 7.0 to 8.0.

5. The process according to claim 4 wherein said slurry is cooled to a temperature in the range −5° to +5° C. before and during filtration.

6. The process according to claim 5 wherein the dicyanopiperazine filter cake is washed free of adherent salt with water cooled to below 5° C.

7. The process according to claim 1 wherein a solution of piperazine in water is reacted with two moles of cyanogen chloride injected below the surface of said solution per mole of contained piperazine while maintaining the temperature of the resulting reaction mixture within the range 30° to 50° C. and the pH within the range 7.0 to 8.0 by the addition as required, of a concentrated solution of NaOH; cooling the resulting slurry of dicyanopiperazine to a temperature in the range −5° to +5° C.; filtering the cooled slurry to separate the dicyanopiperazine from the salt water and washing the dicyanopiperazine filter cake free from adherent salt with water cooled to below +5° C.

8. The process according to claim 1 which is performed by continuously introducing into a reaction space an aqueous solution of piperazine and NaOH, in a proportion of two equivalents of NaOH per mole of piperazine and continuously sparging gaseous cyanogen chloride into said solution at a rate equilibrated to maintain the pH of the reaction mixture in the range 7.0 to 8.0 while maintaining the reaction mixture within the temperature range 30° to 50° C.; continuously transferring the reaction mixture to a crystallizing space within which the slurry reaction mixture is cooled to a temperature range of $-5°$ to $+5°$ C.; filtering the cooled slurry to separate the dicyanopiperazine from the saline liquid, washing the dicyanopiperazine free from adhering salt with water cooled to below about $+5°$ C., drying the washed product and recovering the dicyanopiperazine.

* * * * *